United States Patent
Arbiser

(10) Patent No.: US 9,567,291 B2
(45) Date of Patent: Feb. 14, 2017

(54) N-(4-(BIS(4-(DIMETHYLAMINO)PHENYL) METHYLENE)-8-(DIMETHYLAMINO)

(71) Applicant: EMORY UNIVERSITY, Atlanta, GA (US)

(72) Inventor: Jack Arbiser, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/786,580

(22) PCT Filed: Apr. 25, 2014

(86) PCT No.: PCT/US2014/035470
§ 371 (c)(1),
(2) Date: Oct. 23, 2015

(87) PCT Pub. No.: WO2014/176510
PCT Pub. Date: Oct. 30, 2014

(65) Prior Publication Data
US 2016/0102048 A1 Apr. 14, 2016

Related U.S. Application Data

(60) Provisional application No. 61/815,877, filed on Apr. 25, 2013.

(51) Int. Cl.
| | | |
|---|---|---|
| C07C 251/30 | (2006.01) |
| A61K 31/15 | (2006.01) |
| A61K 45/06 | (2006.01) |
| C09B 11/12 | (2006.01) |
| C07C 251/22 | (2006.01) |
| C07D 223/28 | (2006.01) |

(52) U.S. Cl.
CPC ............. *C07C 251/30* (2013.01); *A61K 31/15* (2013.01); *A61K 45/06* (2013.01); *C07C 251/22* (2013.01); *C07D 223/28* (2013.01); *C09B 11/12* (2013.01); *C07C 2102/10* (2013.01)

(58) Field of Classification Search
None
See application file for complete search history.

(56) References Cited

U.S. PATENT DOCUMENTS

| 8,435,979 B2* | 5/2013 | Arbiser ................ A61K 31/47 514/217 |
| 8,436,195 B2 | 5/2013 | Kutushov |
| 2002/0123531 A1 | 9/2002 | Indig |
| 2004/0132830 A1 | 7/2004 | Finer |
| 2009/0176745 A1* | 7/2009 | Arbiser ............... A61K 31/136 514/114 |
| 2010/0189762 A1* | 7/2010 | Arbiser ................ A61K 31/47 424/423 |
| 2012/0190847 A1* | 7/2012 | Arbiser ............... A61K 31/136 540/592 |

FOREIGN PATENT DOCUMENTS

| WO | 9734589 | 9/1997 |
| WO | 9857922 | 12/1998 |
| WO | 0030632 | 2/2000 |

OTHER PUBLICATIONS

Rabbani et al., Int. J. Cancer (1995), 63, 840-845.*
Carvalho et al. "Triphenylmethane Derivatives Have High In Vitro and In Vivo Activity against the Main Causative Agents of Cutaneous Leishmaniasis" PLoS ONE, 2013; 8(1): e51864.
Klingenberg et al. "The NADPH oxidase inhibitor imipramine-blue in the treatment of Burkitt lymphoma" Mol Cancer Ther., 2014; 13(4): 833-841.
Munson et al. "Anti-invasive small molecule, Imipramine Blue (IB), inhibits invasion of glioma" Sci Transl Med, 2014; 4: 127ra36.
Rabbani et al. "Prevention of prostate-cancer metastasis in vivo by a novel synthetic inhibitor of urokinase-type plasminogen activator (uPA)" Int. J. Cancer, 1995; 63: 840-845.

\* cited by examiner

*Primary Examiner* — Brian J Davis
(74) *Attorney, Agent, or Firm* — Emory Patent Group

(57) ABSTRACT

This disclosure relates to N-(4-(bis(4-(dimethylamino)phenyl)methylene)-8 -(dimethylamino)naphthalen-1(4H)-ylidene)-N-methylmethanaminium, derivatives, and uses related thereto. In certain embodiments, the disclosure relates to compounds of formula I. In certain embodiments, the disclosure relates to methods of treating or preventing Nox related diseases and conditions comprising administering an effective amount of compounds disclosed herein to a subject in need thereof. In certain embodiments, the Nox related disease or condition is cancer.

11 Claims, 5 Drawing Sheets

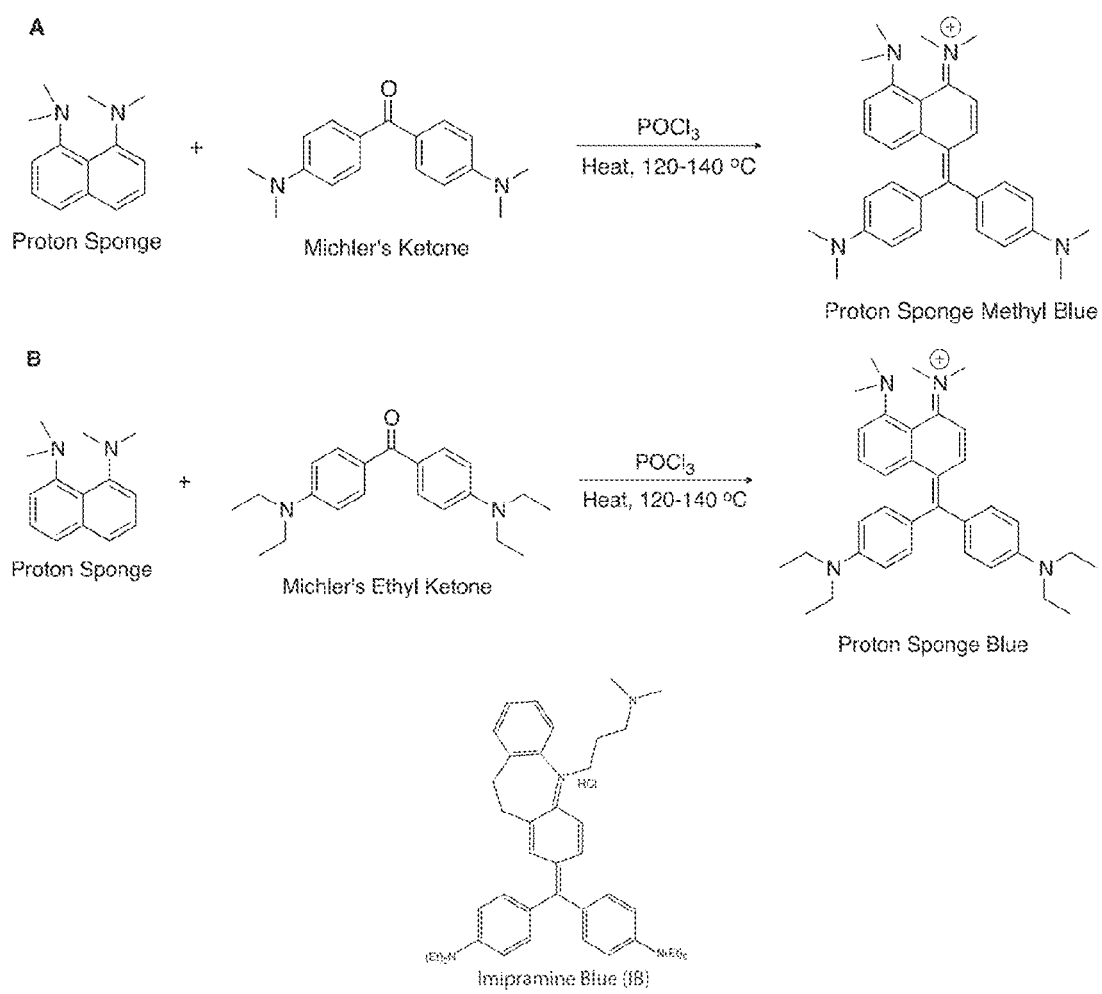
FIG. 2A-B

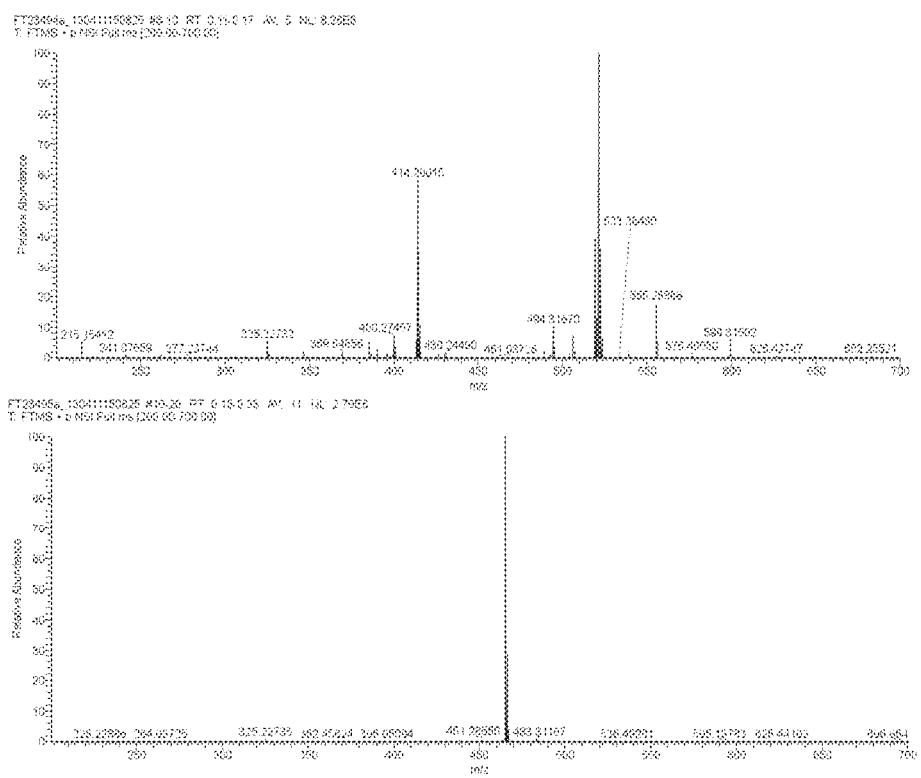
FIG. 3A-B

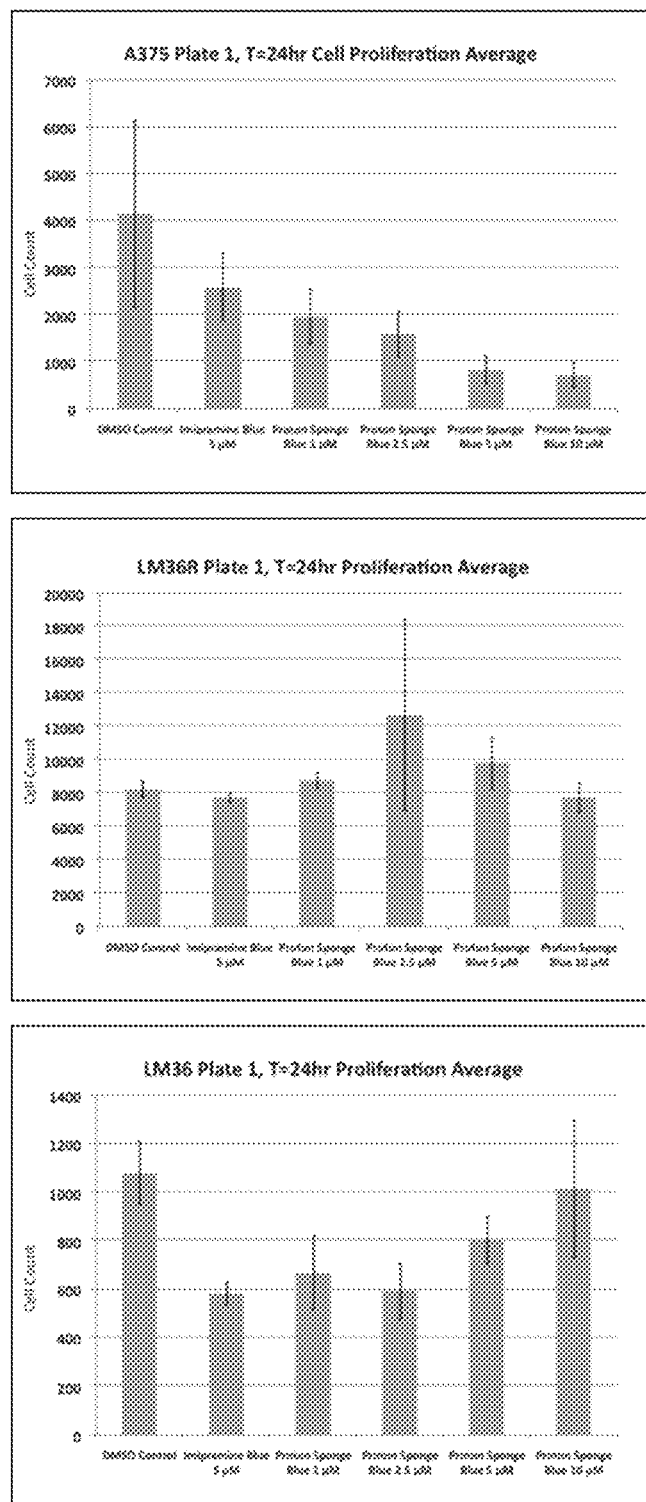
FIG. 4A-C

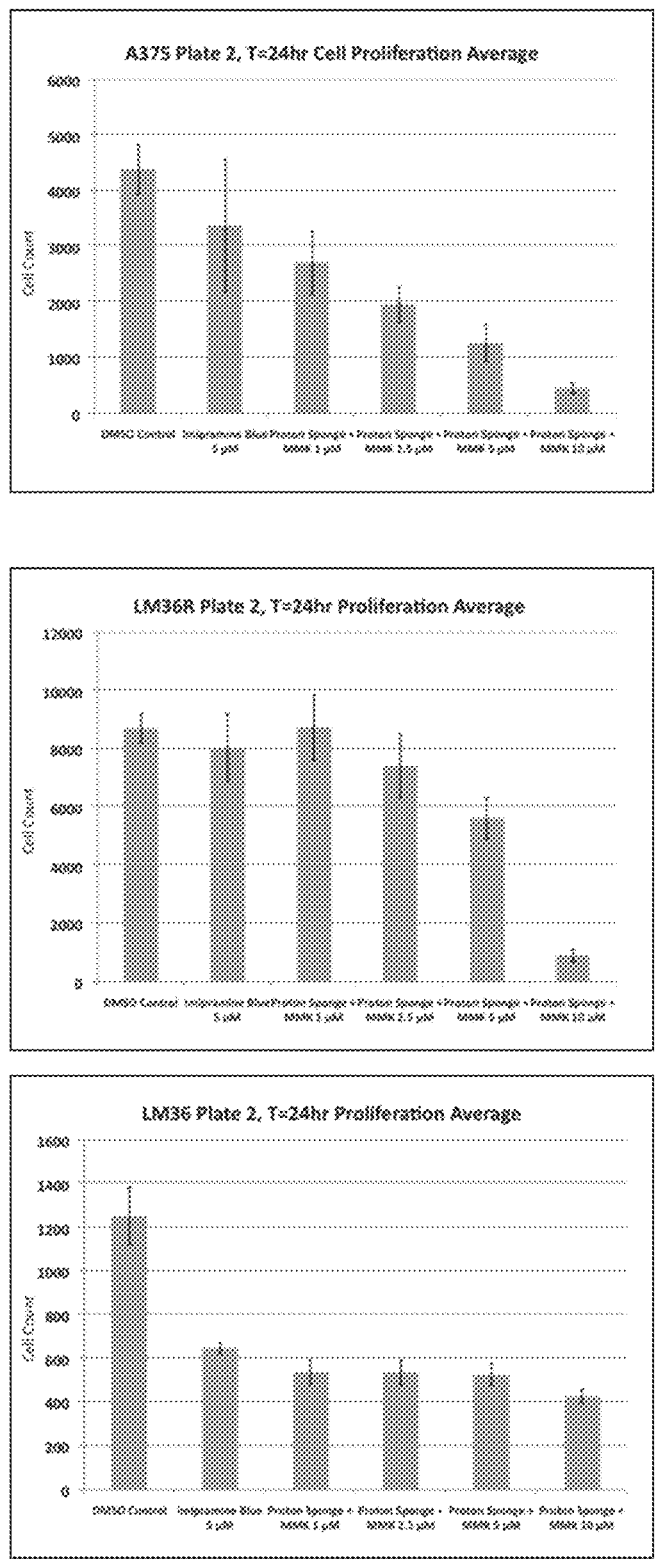
FIG. 5A-C

N-(4-(BIS(4-(DIMETHYLAMINO)PHENYL) METHYLENE)-8-(DIMETHYLAMINO)

CROSS REFERENCE TO RELATED APPLICATIONS

This Application is a National Stage Entry under 35 USC 371 and claims priority to pending International Application No. PCT/US14/35470 filed Apr. 25, 2014, and claims priority to U.S. 61/815,877 filed Apr. 25, 2013, both hereby incorporated by reference in their entirety.

BACKGROUND

The invasive nature of glioblastoma (GBM) represents a major clinical challenge contributing to poor outcomes. Invasion of GBM into healthy tissue restricts chemotherapeutic access and complicates surgical resection. Munson et al., report an anti-invasive small molecule, Imipramine Blue (IB), inhibits invasion of glioma. Sci Transl Med 4, 127ra36 (2012). IB inhibits NADPH (reduced form of nicotinamide adenine dinucleotide phosphate) oxidase-mediated reactive oxygen species generation and alters expression of actin regulatory elements.

Klingenberg et al. report the NADPH oxidase inhibitor imipramine-blue in the treatment of burkitt lymphoma. Mol Cancer Ther. 2014, 13(4):833-41.

See also US20040132830A1, US20090176745A1, U.S. Pat. Nos. 8,435,979B2, 8,436,195B2, WO2000030632A1, WO1998057922A1, and WO1997034589A1.

There remains a need for treatment of cancer that does not have the adverse effects generally caused by the non-selectivity of conventional chemotherapeutic agents.

References cited herein are not an admission of prior art.

SUMMARY

This disclosure relates to N-(4-(bis(4-(dimethylamino) phenyl)methylene)-8-(dimethylamino)naphthalen-1(4H)-ylidene)-N-methylmethanaminium, derivatives, and uses related thereto. In certain embodiments, the disclosure relates to compounds of formula I. In certain embodiments, the disclosure relates to methods of treating or preventing cancer comprising administering an effective amount of compounds disclosed herein to a subject in need thereof.

In certain embodiments, the disclosure relates to compounds comprising Formula I:

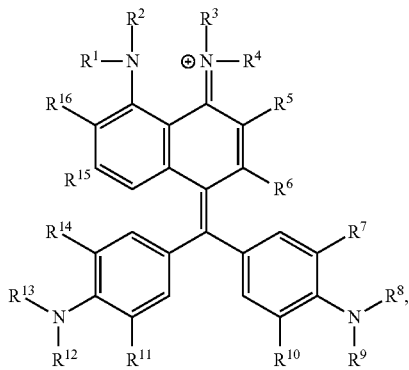

Formula I prodrugs, derivatives, esters, or salts thereof wherein, as described herein.

In certain embodiments, the disclosure related to a pharmaceutical composition comprising N-(4-(bis(4-(dimethylamino)phenyl)methylene)-8-(dimethylamino) naphthalen-1 (4H)-ylidene)-N-methylmethanaminium or N-(4-(bis(4-(diethylamino)phenyl)methylene)-8-(dimethylamino) naphthalen-1(4H)-ylidene)-N-methylmethanaminium, derivatives, or salts thereof and a pharmaceutically acceptable excipient.

In certain embodiments, the disclosure relates to a pharmaceutical composition further comprising a second therapeutic agent.

In certain embodiments, second therapeutic agent is an anti-cancer agent.

In certain embodiments, the disclosure relates to a method of treating or preventing cancer comprising administering an effective amount of a compound to a subject in need thereof.

In certain embodiments, the subject is diagnosed with or at risk of cancer.

In certain embodiments, the compound is administered in combination with a second therapeutic agent.

In certain embodiments, the cancer is selected from bladder cancer, lung cancer, breast cancer, melanoma, colon and rectal cancer, non-hodgkin lymphoma, burkitt lymphoma, endometrial cancer, pancreatic cancer, kidney cancer, prostate cancer, leukemia, thyroid cancer, and brain cancer.

In certain embodiments, the compound is administered in combination with a second anticancer agent.

BRIEF DESCRIPTION OF FIGURES

FIG. 2 illustrates the chemical synthesis of Proton Sponge Methyl Blue (A) and Proton Sponge Blue (B). Both reactions utilize a similar mechanism that involves $POCl_3$ acting as a catalyst.

FIG. 3 illustrates mass spectrometry results for (A) Proton Sponge Blue suggests an exact mass of 521.3681 g/mol and an exact mass of 465.3010 g/mol for (B) Proton Sponge Methyl Blue.

FIG. 4 illustrates cell proliferation assay results for PSB compared to IB and DMSO. (A) PSB inhibits A375 proliferation in a concentration-dependent fashion and is more potent than IB. Such a trend is not observed in LM36R (B) or LM36 (C) assays where IB exhibits stronger anti-proliferative effects.

FIG. 5 illustrates cell proliferation assay results for PSMB compared to IB and DMSO. PSMB has anti-proliferative effects that operate in a concentration-dependent fashion in A375 (A), LM36R (B) and LM36 (C) cell lines. In each of the cell lines, PSMB exhibits more potent inhibition than IB. Please note that Proton Sponge+MMK is the same as PSMB.

DETAILED DESCRIPTION

Figure 1:
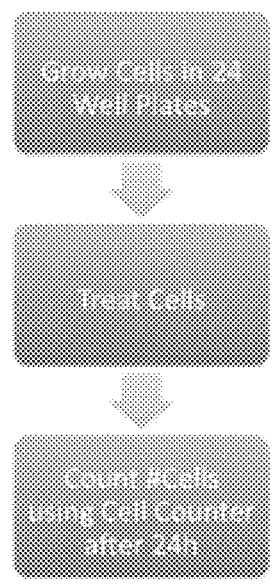
FIG. 1 illustrates the cell proliferation assay procedure. $5 \times 10^4$ cells were seeded in 24-well plates and incubated for 24 h. Stock solutions of PSB, PSMB, and IB were diluted into 5 mL of appropriate media samples for each treatment concentration (1 µM, 2.5 µM, etc). One mL was then added to each of the four wells per treatment concentration. Cells were incubated for 24 h in standard conditions. Cells were then washed with Phosphate Buffered Saline (Sigma Aldrich) and harvested by trypsinization (0.5 mL/well). Cells were incubated for 10 minutes in standard conditions and diluted into a 10 mL isotone solution. The isotone solution was subsequently placed into a cell counter, providing a count that represented 1/20 the number of cells per well.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

As used herein, "alkyl" means a noncyclic straight chain or branched, unsaturated or saturated hydrocarbon such as those containing from 1 to 10 carbon atoms, typically 1 to 6 carbon atoms. Within any embodiments, herein alkyl may refer to an alkyl with 1 to 6 carbons ($C_{1-6}$alkyl). Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—$CH_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—$CH_3$).

"Alkanoyl" refers to an alkyl as defined above attached through a carbonyl bride (i.e., —(C=O)alkyl). "Alkyloxycarbonyl" refers to an alkyl as defined above attached through a carboxy bridge (i.e., —(C=O)Oalkyl.

"Alkylcarbamoyl" refers to an alkyl as defined above attached through a carbonyl bridge (i.e., —(C=O)NHalkyl).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfonamide" refers to an alkyl as defined above attached through a sulfamoyl bridge (i.e., —S(=O)$_2$NHalkyl), and an "Arylsulfonamide" refers to an alkyl attached through a sulfamoyl bridge (i.e., —S(=O)$_2$NHaryl).

"Alkylsulfinyl" refers to an alkyl as defined attached through a sulfinyl bridge (i.e. —S(=O)alkyl).

The terms "halogen" and "halo" refer to fluorine, chlorine, bromine, and iodine. The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing a amino group with a hydroxyl group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

Throughout the specification, groups and substituents thereof may be chosen to provide stable moieties and compounds.

Compounds

In certain embodiment this disclosure relates to compounds comprising Formula I:

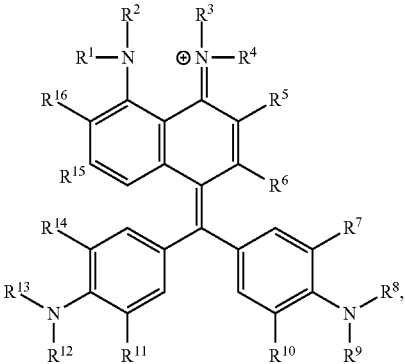

Formula I prodrugs, derivatives, esters, or salts thereof wherein, $R^1$, $R^2$, $R^3$, and $R^4$ are methyl, propyl, or optionally substituted with one or more, the same or different, $R^{20}$ or $R^{21}$;

$R^5$, $R^6$, $R^7$, $R^{10}$, $R^{11}$, $R^{14}$, $R^{15}$, and $R^{16}$ are individually and independently alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^5$, $R^6$, $R^7$, $R^{10}$, $R^{11}$, $R^{14}$, $R^{15}$, and $R^{16}$ are optionally substituted with one or more, the same or different, $R^{20}$;

$R^8$, $R^9$, $R^{12}$, and $R^{13}$ are methyl, ethyl, propyl, or optionally substituted with one or more, the same or different, $R^{20}$ or $R^{21}$;

$R^{20}$ is alkyl, halogen, nitro, cyano, hydroxy, amino, mercapto, formyl, carboxy, carbamoyl, alkoxy, alkanoyl, alkylthio, alkylamino, (alkyl)2amino, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, Nmethyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N -dimethylsulfamoyl, N,N-diethylsulfamoyl, N-methyl-N-ethylsulfamoyl, carbocyclyl, aryl, or heterocyclyl.

In certain embodiments, $R^1$, $R^2$, $R^3$ and $R^4$ are methyl.
In certain embodiments, $R^8$, $R^9$, $R^{12}$ and $R^{13}$ are methyl.
In certain embodiments, $R^8$, $R^9$, $R^{12}$ and $R^{13}$ are ethyl.

Combination Therapies

In certain embodiments, cancer therapeutic strategies entail pharmaceutical compositions comprising a compound disclosed herein administered in combination with a second anti-cancer agent such as temozolomide, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

The cancer treatments disclosed herein can be applied as a sole therapy or can involve, conventional surgery or radiotherapy or chemotherapy. Such chemotherapy can include one or more of the following categories of anti-tumor agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon (ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family for example EGFR family tyrosine kinase inhibitors such as: N-(3-chloro-4-fluorophenyl)-7-methoxy-6-(3-morpholinopropoxy)quinazolin-4-a mine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet -derived growth factor family and for example inhibitors of the hepatocyte growth factor family, for example inhibitors of phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-RAS antisense; and (viii) immunotherapy approaches, including for example ex-vivo and in-vivo approaches to increase the immunogenicity of subject tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies, and approaches using the immunomodulatory drugs thalidomide and lenalidomide [Revlimid®].

The combination therapy also contemplates use of the disclosed pharmaceutical compositions with radiation therapy or surgery, as an alternative, or a supplement, to a second therapeutic or chemotherapeutic agent.

A typical chronic lymphocytic leukemia (CLL) chemotherapeutic plan includes combination chemotherapy with chlorambucil or cyclophosphamide, plus a corticosteroid such as prednisone or prednisolone. The use of a corticosteroid has the additional benefit of suppressing some related autoimmune diseases, such as immunohemolytic anemia or immune-mediated thrombocytopenia. In resistant cases, single-agent treatments with nucleoside drugs such as fludarabine, pentostatin, or cladribine may be successful. Patients may consider allogeneic or autologous bone marrow transplantation. In certain embodiments, the disclosure contemplates combination treatments using compounds disclosed herein in combination with chloroambucil, cyclophosphamide, prednisone, prednisolone, fludarabine, pentostatin, and/or cladribine or combinations thereof.

Treatment of acute lymphoblastic leukemia typically includes chemotherapy to bring about bone marrow remission. Typical regiments include prednisone, vincristine, and an anthracycline drug, L-asparaginase or cyclophosphamide. Other options include tprednisone, L-asparaginase, and vincristine. Consolidation therapy or intensification therapy to eliminate any remaining leukemia may include antimetabolite drugs such as methotrexate and 6-mercaptopurine (6-MP). In certain embodiments, the disclosure contemplates combination treatments using compounds disclosed herein in combination with COP, CHOP, R-CHOP, imatinib, alemtuzumab, vincristine, L-asparaginase or cyclophosphamide, methotrexate and/or 6-mercaptopurine (6-MP). COP refers to a chemotherapy regimen used in the treatment of lymphoma of cyclophosphamide, vincristine, and prednisone or prednisolone and optionally hydroxydaunorubicin (CHOP) and optionally rituximab (R-CHOP).

In certain embodiments, the disclosure relates to the treatment or prevention of bacterial infection comprising administering a compound disclosed herein to a subject in need thereof optionally in combination with anti-bacterial agent such as those selected from the group comprising of sulfonamides, diaminopyrimidines, quinolones, beta-lactam antibiotics, cephalosporins, tetracyclines, nitrobenzene derivatives, aminoglycosides, macrolide antibiotics, polypeptide antibiotics, nitrofuran derivatives, nitroimidazoles, nicotinin acid derivatives, polyene antibiotics, imidazole derivatives or glycopeptide, cyclic lipopeptides, glycylcyclines and oxazolidinones.

In further embodiments, these antibiotics include but are not limited to sulphadiazine, sulfones—[dapsone (DDS) and paraaminosalicyclic (PAS)], sulfanilamide, sulfamethizole, sulfamethoxazole, sulfapyridine, trimethoprim, pyrimethamine, nalidixic acids, norfloxacin, ciprofloxin, cinoxacin, enoxacin, gatifloxacin, gemifloxacin, grepafloxacin, levofloxacin, lomefloxacin, moxifloxacin, ofloxacin, pefloxacin, sparfloxacin, trovafloxacin, penicillins (amoxicillin, ampicillin, azlocillin, carbenicillin, cloxacillin, dicloxacillin, flucloxacillin, hetacillin, oxacillin, mezlocillin, penicillin G, penicillin V, piperacillin), cephalosporins (cefacetrile, cefadroxil, cefalexin, cefaloglycin, cefalonium, cefaloridin, cefalotin, cefapirin, cefatrizine, cefazaflur, cefazedone, cefazolin, cefradine, cefroxadine, ceftezole, cefaclor, cefonicid, ceforanide, cefprozil, cefuroxime, cefuzonam, cefmetazole, cefoteta, cefoxitin, cefcapene, cefdaloxime, cefdinir, cefditoren, cefetamet, cefixime, cefmenoxime, cefodizime, cefoperazone, cefotaxime, cefotiam, cefpimizole, cefpiramide, cefpodoxime, cefteram, ceftibuten, ceftiofur, ceftiolen, ceftizoxime, ceftriaxone, cefoperazone, ceftazidime, cefepime), moxolactam, carbapenems (imipenem, ertapenem, meropenem) monobactams (aztreonam) oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomicin, neomycin, netilmicin, streptomycin, tobramycin, azithromycin, clarithromycin, dirithromycin, erythromycin, roxithromycin, telithromycin, polymyxin-B, colistin, bacitracin, tyrothricin notrifurantoin, furazolidone, metronidazole, tinidazole, isoniazid, pyrazinamide, ethionamide, nystatin, amphotericin-B, hamycin, miconazole, clotrimazole, ketoconazole, fluconazole, rifampacin, lincomycin, clindamycin, spectinomycin, chloramphenicol, clindamycin, colistin, fosfomycin, loracarbef, metronidazole, nitrofurantoin and combinations thereof.

In certain embodiments, the disclosure relates to treating inflammation or an inflammatory disease or condition by administering an effective amount of a compound disclosed herein in combination with an anti-inflammatory agent such as salicylates, aspirin (acetylsalicylic acid), diflunisal, salsalate, propionic acid derivatives, ibuprofen, dexibuprofen, naproxen, fenoprofen, ketoprofen, dexketoprofen, flurbiprofen, oxaprozin, loxoprofen, acetic acid derivatives, indomethacin, tolmetin, sulindac, etodolac, ketorolac, diclofenac, nabumetone, enolic acid (oxicam) derivatives, piroxicam, meloxicam, tenoxicam, droxicam, lornoxicam, isoxicam, fenamic acid derivatives (fenamates), mefenamic acid, meclofenamic acid, flufenamic acid, tolfenamic acid, selective COX-2 inhibitors (voxibs), celecoxib, rofecoxib, valdecoxib, parecoxib, lumiracoxib, etoricoxib, firocoxib, sulphonanilides, nimesulide, licofelone, and combinations thereof.

Pharmaceutical Compositions

The compounds of the present disclosure can be administered to a subject either alone or as a part of a pharmaceutical composition.

This application claims as a novel pharmaceutical composition, all the claimed compounds combined with one or more pharmaceutical agents, as well as the combination of one or more pharmaceutical agents with any compound in the family represented by Formula I.

Pharmaceutically acceptable salts, solvates and hydrates of the compounds listed are also useful in the method of the disclosure and in pharmaceutical compositions of the disclosure.

The pharmaceutical compositions of the present disclosure can be administered to subjects either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo) and injectable organic esters such as ethyl oleate. Proper fluidity can be maintained, for example, by the use of a coating such as lecithin, by the maintenance of the required particle size in the case of dispersions and by the surfactants.

These compositions may also contain adjuvants such as preserving, emulsifying, and dispensing agents. Prevention of the action of microorganisms may be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar and as high molecular weight polyethylene glycols, and the like.

Solid dosage forms such as tablets, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner Examples of embedding compositions which can be used are polymeric substances and waxes. The active compounds can also be used in micro-encapsulated form, if appropriate, with one or more of the above-mentioned excipients. Controlled slow release formulations are also preferred, including osmotic pumps and layered delivery systems.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, viscoleo, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated iso-stearyl alcohols, polyoxyethylene sorbitol and sorbitan esters, microcrystalline cellulose, aluminum metahydroxide, bentonite agar-agar and tragacanth, or mixtures of these substances, and the like.

Compositions for rectal administrations are preferably suppositories which can be prepared by mixing the compounds of the present disclosure with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a compound of this disclosure include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this disclosure.

Pharmaceutical compositions disclosed herein can be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure can also form internal salts, and such compounds are within the scope of the disclosure. When a compound contains a hydrogen-donating heteroatom (e.g. NH), salts are contemplated to cover isomers formed by transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases can also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein can be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Examples of structuring a compound as prodrugs can be found in the book of Testa and Caner, Hydrolysis in Drug and Prodrug Metabolism, Wiley (2006) hereby incorporated by reference. Typical prodrugs form the active metabolite by transformation of the prodrug by hydrolytic enzymes, the hydrolysis of amides, lactams, peptides, carboxylic acid esters, epoxides or the cleavage of esters of inorganic acids.

Pharmaceutical compositions typically comprise an effective amount of a compound and a suitable pharmaceutical acceptable carrier. The preparations can be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences. It is well known that ester prodrugs are readily degraded in the body to release the corresponding alcohol. See e.g., Imai, Drug Metab Pharmacokinet. (2006) 21(3):173-85, entitled "Human carboxylesterase isozymes: catalytic properties and rational drug design.

Generally, for pharmaceutical use, the compounds can be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the at least one compound of the disclosure e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount," by which it is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the subject per day, more often between 0.1 and 500 mg, such as between 1 and 250 mg, for example about 5, 10, 20, 50, 100, 150, 200 or 250 mg, per kilogram body weight of the subject per day, which can be administered as a single daily dose, divided over one or more daily doses. The amount(s) to be administered, the route of administration and the further treatment regimen can be determined by the treating clinician, depending on factors such as the age, gender and general condition of the subject and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Formulations containing one or more of the compounds described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which can include plasticizers, pigments, colorants, stabilizing agents, and glidants. Delayed release, extended release, and/or pulsatile release dosage formulations can be prepared as described in standard references such as "Pharmaceutical dosage form tablets," eds. Liberman et al. (New York, Marcel Dekker, Inc., 1989), "Remington—The science and practice of pharmacy," 20th ed., Lippincott Williams & Wilkins, Baltimore, Md., 2000, and "Pharmaceutical dosage forms and drug delivery systems," 6th Edition, Ansel et al., (Media, P A: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material can contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants can be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine and lauryl sulfobetaine.

If desired, the tablets, beads, granules, or particles can also contain minor amount of nontoxic auxiliary substances such as wetting or emulsifying agents, dyes, pH buffering agents, or preservatives.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers Ammonio methacrylate copolymers are fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit®RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS can be mixed together in any desired ratio in order to ultimately obtain a sustained-release formulation having a desirable dissolution profile. Desirable sustained-release multiparticulate systems can be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers can also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition can be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and can be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit®. (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials can also be used. Multi-layer coatings using different polymers can also be applied.

The coating composition can include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates can also be used. Pigments such as titanium dioxide can also be used. Small quantities of an anti-foaming agent, such as a silicone (e.g., simethicone), can also be added to the coating composition.

Alternatively, each dosage unit in the capsule can comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that can or cannot include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles can be formulated to provide immediate release, beads and granules are generally employed to provide delayed release.

Methods of Using the Compounds and/or Pharmaceutical Compositions

The compounds described herein, and pharmaceutical compositions including the compounds, can be used to treat cancers. The cancers include those in which one of the Nox enzymes is present in elevated concentrations (i.e., Nox 1, Nox 4, and the like), or those in which cancer growth is mediated by ROS.

Representative disorders that can be treated include neoplasms, such as hemangiomas, and malignant tumors, for example, those which arise in the setting of autocrine loops involving vascular endothelial growth factor (VEGF) and its major mitogenic receptor vascular endothelial growth factor receptor 2. Representative malignant tumors include malignant endothelial tumors such as melanoma.

Representative malignant tumors include malignant endothelial tumors such as melanoma. Additional cancers that can be treated include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., plasma cell leukemia, acute lymphocytic leukemia, acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), including NF-KB mutant and Velcade Resistant lymphoma cells, multiple myeloma, PI3 kinase deficient myeloma, Waldenstrom's macroglobulinemia, and heavy chain disease, and malignant forms of these cancers. Additionally, the compounds can be used in assays involving lymphoblastoid and EBV positive cells.

In one embodiment, the cancer is melanoma, rectal carcinoma, colon carcinoma, breast carcinoma, ovarian carcinoma, small cell lung carcinoma, colon carcinoma, chronic lymphocytic carcinoma, hairy cell leukemia, esophogeal carcinoma, prostate carcinoma, breast cancer, myeloma, or lymphoma. It is believed that these cancers have circulating levels of tNOX (which may include Nox4 or other Nox enzymes) present in the sera of patients suffering from the cancer (see, for example, U.S. Pat. No. 5,605,810, which is hereby incorporated by reference in its entirety).

In one embodiments, the treatment is of glioblastoma (GBM) with compounds disclosed herein, in combination with temozolomide (in a single pharmaceutical product or separate administration) and optionally radiotherapy.

In some embodiments, the patient already has cancer and is undergoing treatment for the cancer, and may or may not have tumor metastasis (i.e., secondary cancer).

In other embodiments, the compounds are active at inhibiting hypoxia-inducible factor HIF2a expression, and this activity aids in the treatment of tumors resistant to standard chemoradiotherapy. Hypoxia-inducible factor HIF2alpha (HIFalphas) regulates the expression of a variety of genes encoding proteins related to angiogenesis and to anaerobic metabolism of cells exposed to hypoxic stress (Koukourakis et al., Int J Radiat Oncol Biol Phys. 2002; 53(5):1192-202.) HIF2a overexpression is significantly associated with high microvessel density (p=0.02, respectively) and with VEGF expression (p=0.005), and VEGF/KDR-activated tumor vasculature is more frequent in HIF2a-overexpressing tumors (p=0.02). High HIF2a levels have been associated with incomplete response to chemoradiation (p=0.02, respectively), and overexpression of HIF2a is related to locally aggressive behavior, intensification of angiogenesis, and resistance to carboplatin chemoradiotherapy.

Imipramine blue was evaluated in a HIF2a expression model, and was shown to inhibit around 90% of the HIF2a expression. In this expression model, WM35 PKB cells are exposed to 5 micromolar of test compounds for 24 hours. At the end of this period, cells are harvested for RNA, which is then reverse transcribed into cDNA, and levels of HIF2a message are quantified using quantitative RT-PCR and corrected for a housekeeping RNA message. As demonstrated using this assay, these compounds can act as direct NADPH oxidase inhibitors, as well as superoxide scavengers that absorb superoxide produced by defective mitochondria or other cellular processes.

The cancer may be manifested in the form of a tumor, such as a tumor of epithelial tissue, lymphoid tissue, connective tissue, bone, or central nervous system.

The compounds can also be used as adjunct therapy in combination with existing therapies in the management of the aforementioned types of cancers. In such situations, it is preferably to administer the active ingredients to in a manner that optimizes effects upon cancer cells, including drug resistant cancer cells, while minimizing effects upon normal cell types. While this is primarily accomplished by virtue of the behavior of the compounds themselves, this can also be accomplished by targeted drug delivery and/or by adjusting the dosage such that a desired effect is obtained without meeting the threshold dosage required to achieve significant side effects.

Specific Disorders Mediated by $Nox_2$ and $Nox_4$ Receptors

Nox2 and Nox4 are NADPH oxidases. Nox2 exists as part of a multiprotein complex, known as cytochrome b558, which includes phox p47phox, p22phox and p21rac, as well as p67phox. Rac may be either rac1 or 2. Nox4 may not require complexing with these proteins.

Nox2 is highly expressed in neutrophils, macrophages and lymphocytes, and may mediate reactive oxygen driven NFkB in inflammatory and neoplastic processes involving neutrophils, macrophages, and lymphocytes, i.e., leukemias and lymphomas.

Nox4 is a widely distributed NADPH oxidase, which is highly expressed in many malignancies, ie melanoma, pancreatic cancer, etc, and generates reactive oxygen that drives NFkB, which then activates antiapoptotic genes such as bcl2 and mcl-1, resulting in resistance to radiation and chemotherapy.

It is proposed that blockade of superoxide will result in decreased expression of NFkB, and will sensitize malignancies to radiation and chemotherapy.

Disorders that are characterized by excess reactive oxygen can be classified into disorders that can be treated and prevented, and patients whose immune systems become more active following administration of the compounds described herein (i.e., immune potentiation). The following disorders can be treated using the compounds described herein:

a) Neoplastic—hemangiomas, melanoma, lung cancer, breast cancer, colon cancer, pancreatic cancer, prostate cancer, ovarian cancer, brain tumors including glioblastoma multiforme, sarcomas, head and neck cancers, hepatocellular carcinoma, nasopharyngeal carcinoma, cervical cancer and precancer, hematologic malignancies including multiple myeloma, myelodysplatic syndrome, acute and chronic leukemias, Hodgkins disease, non hodgkins lymphoma, including diffuse large B cell lymphoma (DLBCL)

b) Inflammatory disorders—psoriasis, atopic dermatitis (eczema), asthma, arthritis (including rheumatoid, psoriatic), inflammatory bowel disease (including Crohns and ulcerative colitis), lupus, multiple sclerosis, Sjogrens disease, gastritis and pernicious anemia, sprue, sarcoidosis, vitiligo, alopecia greata, scleroderma, fibrotic disorders, cirrhosis, coronary artery disease, atherosclerosis, myositis, myocarditis c) Degenerative disease—macular degeneration, Alzheimers disease, parkinsons disease, lewy body dementia, prion mediated disorders, emphysema, cataracts, photoaging of skin, pterygium, osteoporosis, pattern hair loss, hypertension, stroke d) Infectious disease—Bacterial, including Staph, i.e. MRSA, viral (i.e., herpes, HIV, HBV, HCV, HPV, and influenza), and fungal (i.e., *Candida*)

Treatment of Osteoporosis

The compounds described herein can also be used to treat osteoporosis. The cytokine RANKL (receptor activator of NF-κB ligand) causes osteoporosis by activating osteoclasts. The compounds inhibit RANKL activity by potentiating apoptosis, suppresses osteoclastogenesis, and inhibits invasion through modulation of nuclear factor-kappaB activation pathway (see, for example, *Mol Cancer Res.* 2006; 4 (9): 621-33).

Treatment of Inflammatory Disorders

The compounds described herein are useful for treating or preventing inflammatory disorders. Reactive oxygen drives NFkB in inflammatory disorders such as rheumatoid arthritis, asthma, psoriasis, excema, lupus, scleroderma, certain heart diseases such atherosclerosis and coronary artery disease, and the like. Because the compounds are effective at inhibiting production of reactive oxygen species, they are active against inflammatory disorders.

The compounds also inhibit certain inflammatory signals, and can alleviate inflammatory disorders such as inflammatory arthritis by inhibiting these signals.

Rheumatoid arthritis (RA) is considered the most common systemic autoimmune disease, but other disorders, such as hypothyroidism, systemic lupus erythematosus (SLE), and the like can also be treated using the compounds described herein. A number of conditions are associated with chronic inflammation and elevated levels of TNF-α and IL-6, including rheumatoid arthritis, heart disease, and cancer. Numerous gastrointestinal disorders are caused by inflammation, including, but not limited to, Crohn's disease, irritable bowel syndrome, and inflammatory bowel syndrome, and these disorders can also be treated and/or prevented using the compounds described herein.

There is a suggested link between rheumatoid arthritis and chronic inflammation due to the re-activation of Epstein-Barr virus (EBV), which latently infects a proportion of memory B cells in >90% of the world's population. Among the EBV-encoded proteins implicated in viral pathogenesis, considerable attention has focused upon latent membrane protein 1 (LMP1). Of the nine EBV genes expressed as proteins in EBV-transformed cells, LMP1 is the best characterized, and is the only EBV-encoded gene product capable of transforming cells in vitro and in vivo, resulting in the potential for lymphoproliferative changes and malignancy. In addition to its established role in the pathogenesis of B cell lymphoma and other malignancies, EBV infection may be linked to exacerbation of various human autoimmune diseases, including RA and SLE.

The mouse collagen-induced arthritis (CIA) model (Myers, et al., Life Science 61: 1861-1878 (1997)) has many pathologic and immunologic parallels to rheumatoid arthritis, and provides a stable, predictable model for evaluating the therapeutic potential of compounds for treating chronic inflammatory conditions. This model can be used, for example, to evaluate the ability of the compounds described herein to treat and/or prevent these disorders.

Treatment of mouse B cell lines with compounds described herein in vitro can be shown to recapitulate the cytokine profile seen in primary mouse B cells with a concomitant dose-dependent decrease in CD40 and LMP1-mediated NFkB and AP-1 activation. Those compounds which decrease CD40 and LMP1-mediated NFkB and AP-1 activation in a dose-dependent manner will be expected to have anti-inflammatory properties, potentially in both the cognitive phase of the immune response, as well as the effector phase, by inhibiting cytokines that lead to chronic inflammation and additional pathology.

Treatment of Neurodegenerative Disorders and/or Providing Neuroprotection

Reactive oxygen species also induce inflammation and neurodegeneration Inhibition of these species can also result in neuroprotection, including protection from further damage following an ischemic brain injury such as a stroke, or that caused from blunt trauma, and treatment or prevention of neurodegenerative disorders such as retinal degenerations, Alzheimer's disease, senile dementia, pre-senile dementia, Parkinsons disease, Fragile X syndrome, tuberous sclerosis, Huntington's Chorea, multiple sclerosis, and the like.

Reactive oxygen species also drive seizures, and the compounds may ameliorate seizures as well.

Treatment of Vascular Disorders

Vascular diseases such as erectile dysfunction and migraines in which ROS have been implicated may also respond to NADPH oxidase inhibitors. The compounds described herein can be used to treat these vascular diseases.

Atherosclerosis is one vascular disorder known to be treated with NADPH oxidase inhibitors (see, for example, U.S. Pat. No. 5,763,496). Accordingly, the compounds can be used to prevent atherosclerosis and/or inhibit the development of an atherosclerotic plaque.

EXAMPLES

The following examples are provided to illustrate the present invention and should not be considered as limiting the scope thereof.

Treatment of cancer using N-(4-(bis(4-(dimethylamino)phenyl)methylene)-8-(dimethylamino)naphthalen-1(4H)-ylidene)-N-methylmethanaminium PSB and PSMB were synthesized using 1:1 equivalents of Proton Sponge and Michler's Ethyl Ketone and Michler's Ketone, respectively. Both reactions were conducted in a bomb flask under heated conditions (120-140° C.) and utilized $POCl_3$ as the catalyst. The compounds were purified using Thin Layer Chromatography and Silica Column Chromatography. The molecular formula and exact mass were determined by mass spectroscopy of purified samples.

A375 cells were grown in high-glucose Dulbecco's modified Eagle's medium (DMEM) (Mediatech) supplemented with fetal bovine serum (FBS) and penicillin/streptomycin (Sigma-Aldrich) in standard conditions (37° C., 5% $CO_2$, humidified atmosphere). LM36 and LM36R cells were grown in cultured in RPMI medium supplemented with 10% FBS, L-glutamine and antibiotics in standard conditions (37° C., 5% $CO_2$, humidified atmosphere).

The aim of this investigation was to determine the capacity of Proton Sponge Blue (PSB) and Proton Sponge Methyl Blue (PSMB) in cell growth inhibition in various cancer cell lines.

FIGS. 4 and 5 illustrate the results of the cell proliferation assays using PSB and PSMB, respectively, compared to IB and DMSO. PSMB exhibits greater antiproliferative effects than IB, while PSB only exhibits greater antiproliferative effects in A375 cells. While an explanation differentiating the antiproliferative ability of PSB, PSMB, and IB remains to be discovered, it is hypothesized that both the charged nature of the triarylmethane and the steric hindrance of the substituents on the aryl ring work synergistically to control the anti-proliferative activity of the compound.

The invention claimed is:

1. A compound comprising formula I:

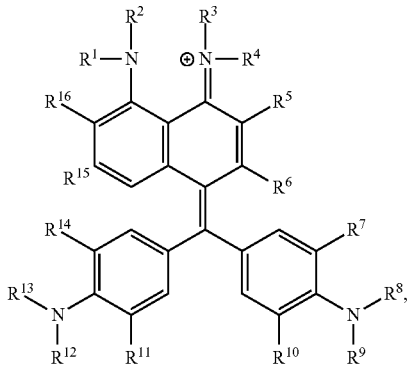

Formula I prodrugs, esters, or salts thereof wherein,
$R^1$, $R^2$, $R^3$, and $R^4$ are methyl, propyl, or optionally substituted with one or more, the same or different, $R^{20}$ or $R^{21}$;
$R^5$, $R^6$, $R^7$, $R^{10}$, $R^{11}$, $R^{14}$, $R^{15}$, and $R^{16}$ are individually and independently alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^5$, $R^6$, $R^7$, $R^{10}$, $R^{11}$, $R^{14}$, $R^{15}$, and $R^{16}$ are optionally substituted with one or more, the same or different, $R^{20}$;
$R^8$, $R^9$, $R^{12}$, and $R^{13}$ are methyl;
$R^{20}$ is alkyl, halogen, nitro, cyano, hydroxy, amino, mercapto, formyl, carboxy, carbamoyl, alkoxy, alkanoyl, alkylthio, alkylamino, (alkyl)2amino, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, Nmethyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound of claim 1, wherein $R^1$, $R^2$, $R^3$ and $R^4$ are methyl.

3. The compound of claim 1, having the formula: N-(4-(bis(4-(dimethylamino)phenyl)methylene)-8-(dimethylamino)naphthalen-1(4H)-ylidene)-N-methylmethanaminium.

4. A pharmaceutical composition comprising a compound of claim 1 or salt thereof and a pharmaceutically acceptable excipient.

5. A pharmaceutical composition of claim 4, further comprising a second therapeutic agent.

6. The pharmaceutical composition of claim 5, wherein the second therapeutic agent is an anti-cancer agent.

7. A method of treating cancer comprising administering an effective amount of a compound in claim 1 to a subject in need thereof.

8. The method of claim 7, wherein the subject is diagnosed with or at risk of cancer.

9. The method of claim 7, wherein the compound is administered in combination with a second therapeutic agent.

10. The method of claim 7, wherein the cancer is selected from bladder cancer, lung cancer, breast cancer, melanoma, colon and rectal cancer, non-hodgkin lymphoma, burkitt lymphoma, endometrial cancer, pancreatic cancer, kidney cancer, prostate cancer, leukemia, thyroid cancer, and brain cancer.

11. The method of claim 7, wherein the compound is administered in combination with a second anticancer agent.

* * * * *